United States Patent
Yang

(10) Patent No.: US 11,242,292 B2
(45) Date of Patent: Feb. 8, 2022

(54) PROCESS FOR PRODUCING HUMIC ACID SALTS WITH FLUIDIZING SOLID PHASE REACTION

(71) Applicant: James Chin Cheng Yang, Houston, TX (US)

(72) Inventor: James Chin Cheng Yang, Houston, TX (US)

(*) Notice: Subject to any disclaimer, the term of this patent is extended or adjusted under 35 U.S.C. 154(b) by 582 days.

(21) Appl. No.: 15/731,032

(22) Filed: Apr. 10, 2017

(65) Prior Publication Data

US 2018/0290941 A1  Oct. 11, 2018
US 2020/0277238 A9  Sep. 3, 2020

Related U.S. Application Data

(60) Provisional application No. 62/331,788, filed on May 4, 2016.

(51) Int. Cl.
*C05F 11/06*  (2006.01)
*C07D 521/00*  (2006.01)
(Continued)

(52) U.S. Cl.
CPC ............ *C05F 11/06* (2013.01); *B01F 13/045* (2013.01); *B01J 2/18* (2013.01); *B01J 8/1836* (2013.01);
(Continued)

(58) Field of Classification Search
CPC combination set(s) only.
See application file for complete search history.

(56) References Cited

U.S. PATENT DOCUMENTS 4,013,440 A * 3/1977 Vale ................. C05C 9/00
                                                71/24
4,069,034 A * 1/1978 Hoover .............. C05B 7/00
                                                71/33
(Continued)

FOREIGN PATENT DOCUMENTS

CN   101544675 A     9/2009
CN   105037746   *  11/2015
(Continued)

OTHER PUBLICATIONS

Variables in Ball Mill Operation (https://www.pauloabbe.com/size-reduction/resources/variables-in-ball-mill-operation) printed Jan. 16, 2021.*

*Primary Examiner* — Kevin R Kruer
(74) *Attorney, Agent, or Firm* — Phan Law Group PLLC

(57) ABSTRACT

The present invention utilizes a high-speed intensive mixer in a fluidizing-type, solid-phase, neutralization reactor to blend solid-state alkali hydroxide with any humic acid sources. The final product is a dry humic acid salt. The purpose of this innovative method is to eliminate a series of complicated unit operations commonly employed by the traditional process. These removed steps may include dissolving caustic soda, mixing in a paste-like formation, extrusion, granulation, drying, and grinding, etc. The invention contributes to a simplified flowsheet, resulting in sharply reduced equipment investment, plant space, and labor and energy costs. All of these factors coupled with increased productivity will drastically lower the overall production cost. Also, the reduction of dust pollution will greatly minimize the impact in environmental protection and safety issues.

11 Claims, 4 Drawing Sheets

(51) Int. Cl.
  *B01J 8/18*   (2006.01)
  *C05F 11/02*  (2006.01)
  *B01J 19/18*  (2006.01)
  *B01F 13/04*  (2006.01)
  *B01J 2/18*   (2006.01)
  *B01J 8/42*   (2006.01)

(52) U.S. Cl.
  CPC .............. *B01J 8/42* (2013.01); *B01J 19/1806* (2013.01); *C05F 11/02* (2013.01); *C07D 521/00* (2013.01)

(56) References Cited

U.S. PATENT DOCUMENTS

| | | | | |
|---|---|---|---|---|
| 4,918,059 | A | * | 4/1990 | Seubert .................. A61K 35/10 514/33 |
| 7,204,660 | B2 | * | 4/2007 | Shulgin .................... B09C 1/08 405/128.75 |
| 7,390,470 | B2 | * | 6/2008 | Anderson ............ B01D 53/526 423/220 |
| 8,758,473 | B2 | * | 6/2014 | Dementjev ............. C05F 11/02 71/24 |

FOREIGN PATENT DOCUMENTS

| | | |
|---|---|---|
| CN | 105037746 A | 11/2015 |
| TW | 201639903 A | 11/2016 |
| WO | 2010/094985 A1 | 8/2010 |

\* cited by examiner

PROCESS FOR PRODUCING HUMIC ACID SALTS WITH FLUIDIZING SOLID PHASE REACTION

BACKGROUND AND SUMMARY OF THE INVENTION

Traditional methods for production of humic acid salts involve complicated unit operations that are costly and usually cause serious environmental issues. This invention uses a high-speed intensive mixer to promote chemical reaction between alkali hydroxide (including potassium hydroxide, sodium hydroxide, or ammonium hydroxide solution, etc.) and any substances containing humic acid. The new process quickly makes a dry product in a solid-phase, fluidized-bed type reactor and can replace the traditional manufacturing procedure with significantly higher efficiency and cost benefits. It also addresses the common public concerns on the safety and pollution problems.

This invention uses only a high-speed intensive mixer to produce the same final products by a single step, completing any of following chemical reactions:

$$R-COOH+NaOH \rightarrow R-COONa+H_2O$$

$$R-COOH+KOH \rightarrow R-COOK+H_2O$$

$$R-COOH+NH_4OH \rightarrow R-COONH4+H_2O$$

The basic principle of the present invention is different from the traditional fluidized bed. The present invention only utilizes high-speed agitation, instead of large amounts of gas, to fluidize solid powder. In practice, one or more alkali hydroxide (including potassium hydroxide, sodium hydroxide, or ammonium hydroxide solution, etc.) can be added to react with any humic acid source.

DETAILED DESCRIPTION OF THE INVENTION

Typical flow charts of the above reactions can be shown in FIGS. 1 to 4 in which the major pieces of equipment are numerically marked and identified as follows:

(1) Unloading hopper,
(2) Pneumatic conveyer,
(3) Premixing feed tank,
(4) Automatic weighing machine,
(5) Solid-phase reactor,
(6) Intermediate tank,
(7) Cyclone separator,
(8) Dust collector,
(9) Storage tank,
(10) Bagging machine,
(11) Blower,
(12) Ammonium hydroxide feeding tank,
(13) Dust collector, and
(14) Seal box.

Figure 1:
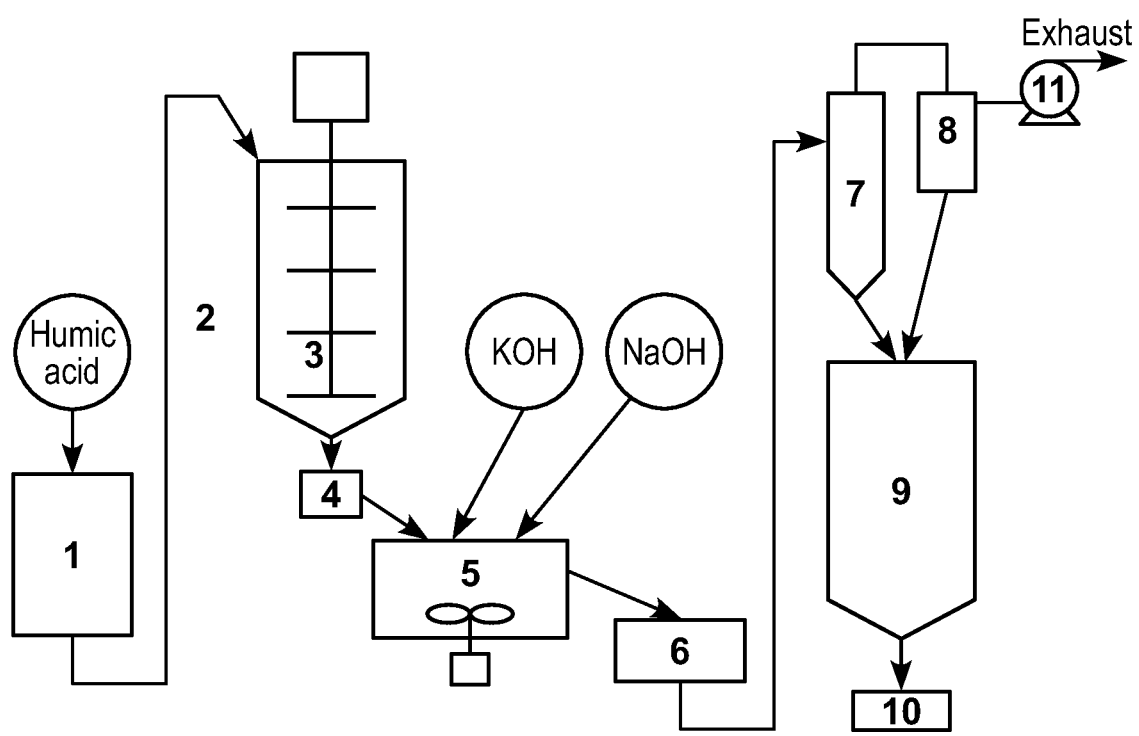
FIG. 1 is a flow chart of a caustic humate manufacturing process by solid phase reaction.

FIG. 1 shows a flow chart of a caustic humate manufacturing process by solid-phase reaction. The process includes the steps below:

1. Feed humic acid to a mixer (3) by pneumatic conveyor (2) to premix the humic acid thoroughly.
2. Feed a fixed amount of the premixed humic acid into the solid-phase reactor (5) to agitate with a high-speed mixer.
3. Slowly add the solid-state alkali hydroxide into the mixer (5) at a given rate.
4. Continue the high-speed agitation while proceed to complete mixing, reaction, and drying.
5. Unload the produced caustic humate salt into the intermediate tank (6) for cooling down, then transfer it to a storage tank (9) by pneumatic conveyor.

Figure 2:
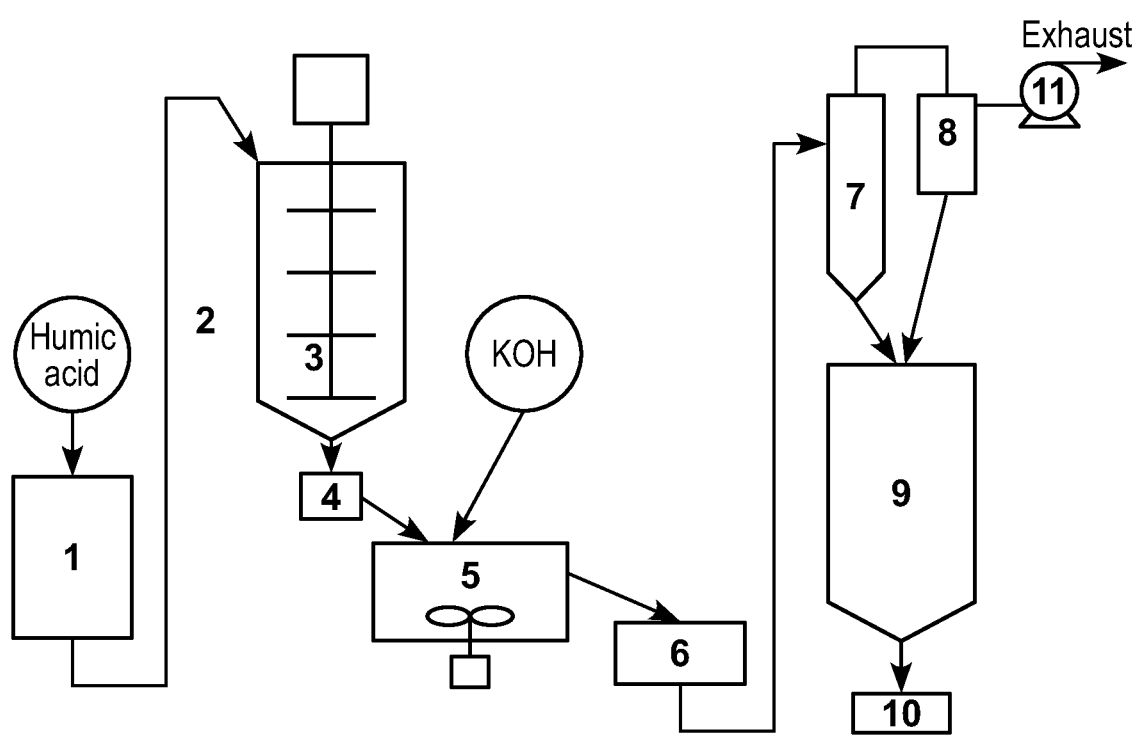
FIG. 2 is a flow chart of a potassium humate manufacturing process by solid phase reaction.

FIG. 2 is a flow chart of a potassium humate manufacturing process by solid-phase reaction. The process includes the steps below:

1. Feed humic acid to a mixer (3) by pneumatic conveyor (2) to premix the humic acid thoroughly.
2. Feed a fixed amount of the premixed humic acid into the solid-phase reactor (5) to agitate with a high-speed mixer.
3. Slowly add the solid-state potassium hydroxide into the mixer (5) at a given rate.
4. Continue the high-speed agitation while proceed to complete mixing, reaction, and drying.
5. Unload the produced potassium humate salt into the intermediate tank (6) to cool down, then transfer to a storage tank (9) by pneumatic conveyor.

Figure 3:
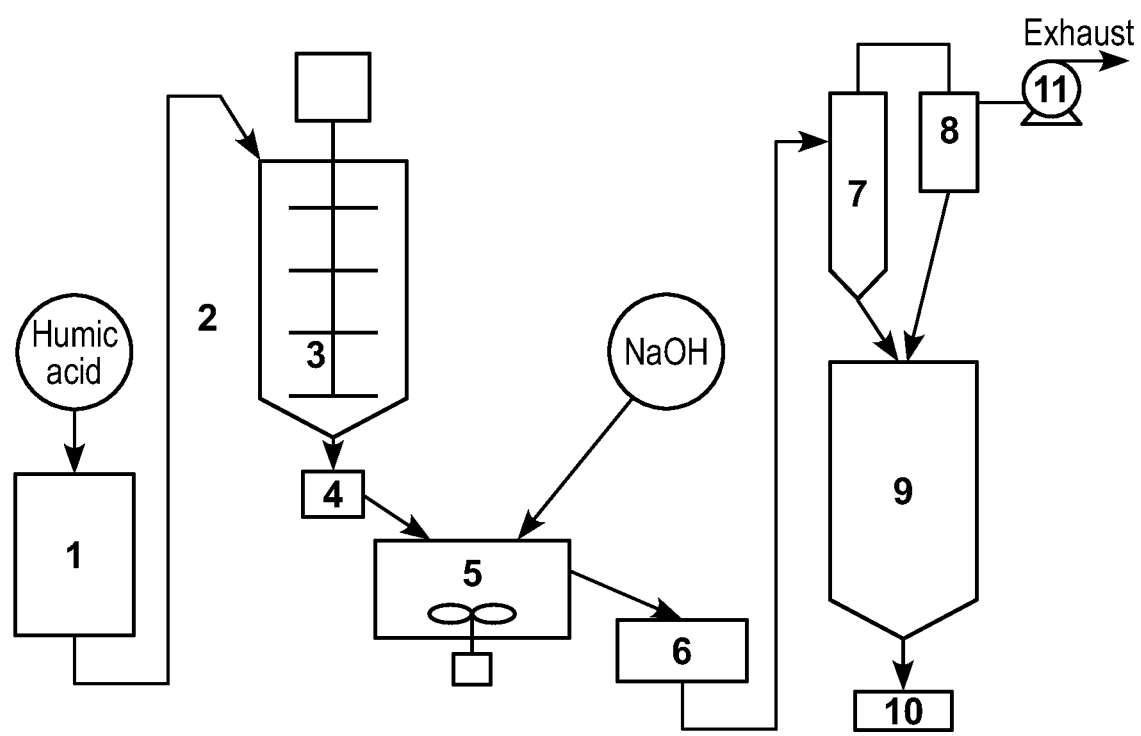
FIG. 3 is a flow chart of a sodium humate manufacturing process by solid phase reaction.

FIG. 3 presents a flow chart of a sodium humate manufacturing process by solid-phase reaction. The process includes the steps below:

1. Feed humic acid to a mixer (3) by pneumatic conveyor (2) to premix the humic acid thoroughly.
2. Feed a fixed amount of the premixed humic acid into the solid-phase reactor (5) to agitate with a high-speed mixer.
3. Slowly add the solid-state sodium hydroxide into the mixer (5) at a given rate.
4. Continue high speed agitation while proceed to complete mixing, reaction, and drying.
5. Unload sodium humate salt produced into intermediate tank (6) for cooling down, then send to storage tank (9) by pneumatic conveyor.

Figure 4:
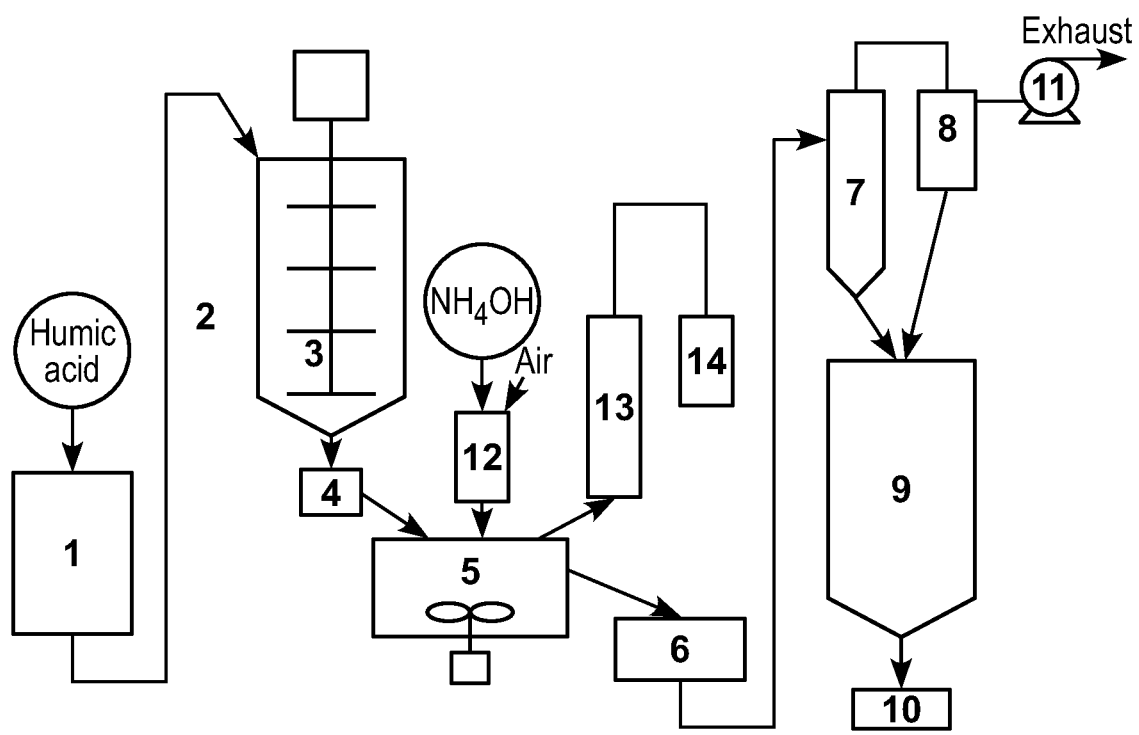
FIG. 4 is a flow chart of an ammonium humate manufacturing process by solid phase reaction.

FIG. 4 shows a flow chart of an ammonium humate manufacturing process by solid-phase reaction. The process includes the steps below:

1. Feed humic acid to a mixer (3) by pneumatic conveyor (2) to premix the humic acid thoroughly.
2. Feed a fixed amount of the premixed humic acid into the solid-phase reactor (5) to agitate with a high speed mixer.
3. Spray a quantitative amount of ammonium hydroxide (12) uniformly into the reactor (5) using high-pressure air.
4. Continue high-speed agitation while proceed to complete mixing, reaction, and drying.
5. Recover ammonia and water vapor evaporated during reaction for recycling.
6. Unload ammonium humate salt produced into intermediate tank (6) for cooling down, then send to storage tank (9) by pneumatic conveyor.

Embodiments of the Invention

By employing a high-speed blender alone, the new process generates a vigorous powder flow and a series of unit operations (including crushing, mixing as well as dissolution, neutralization, and evaporation due to friction heat); the reaction temperature can thus be automatically controlled. The embodiments of this invention include, but is not limited, to the following:

1. A process for producing potassium humate with a solid-phase fluidized bed reaction. The mixture of potassium hydroxide containing 5 to 30% water and humic acid react in a high-speed intensive mixer running at 300-2000 RPM. The agitation is multidirectional and free flowing, and potassium humate is produced by means of high-speed agitation for mixing and neutralization reaction.

2. A process for producing sodium humate with a solid-phase fluidized bed reaction. The mixture of sodium hydroxide containing 5 to 30% water and humic acid react in high-speed intensive mixer running at 300-2000 RPM. The agitation is multi-directional and free flowing, and sodium humate is produced by means of high-speed agitation for mixing and neutralization reaction.

3. A process for producing potassium and sodium humate with a solid-phase fluidized bed reaction. The mixture of potassium hydroxide and sodium hydroxide containing 5 to 30% water and humic acid react in a high-speed intensive mixer running at 300-2000 RPM. The agitation is multi-directional and free flowing, and the mixture of sodium and potassium humate is produced by means of high-speed agitation for mixing and neutralization reaction.

4. A process for producing ammonium humate with a solid-phase fluidized bed reaction. This process uses a high-pressure spray mode to mix ammonium hydroxide with humic acid in a high-speed intensive mixer running at 300-2000 RPM. The agitation is multi-directional and free flowing, and ammonium humate is produced by means of high-speed agitation for mixing and neutralization reaction.

5. In accordance with Embodiments 1 to 4, a manufacturing process utilizes high-speed mixing to mix the mixture of solid containing less than 50% water and water-soluble solid or liquid-mist under fluidizing condition.

6. In accordance with Embodiment 5, the humic acid includes, but is not limit to, brown coal, peat, and weathering coal containing 5-90% humic acid.

7. In accordance with Embodiment 6, the raw materials of humic acid and caustic powder shattered by a mixer can increase the reaction area.

8. Use a high-intensity mixer to achieve uniform quality, while increasing the contact area of the base and reducing the solid-state reaction time.

9. Utilize high-speed stirring action to create sufficient heat by friction between reactant powders.

10. Utilize friction heat generated to liquefy solid alkali.

11. Potassium hydroxide is dissolved and ionized to K (or Na) ions which react with humic acid's COOH radicals ionized from humic acid.

12. Utilize the heat generated by the heat of reaction and friction heat to evaporate water and eliminate the energy required for drying.

13. Use the boiling point of water to make automatic temperature regulation.

Advantages Over the Prior Art

There are many unique technical advantages of the present invention over traditional methods of producing humic acid salts, such as those claimed by Patent CN101544675B. The most noticeable differences are:

1. This invention utilizes only high-speed agitation instead of the standard fluidized-bed, which requires a large amount of gas to fluidize the solid powder.

2. The present invention utilizes reaction heat and friction heat to evaporate excess water for keeping the reaction temperature and drying product simultaneously. The conventional method requires a lot of extra steam to maintain the reaction temperature.

3. The present invention is a dry process, achieving a complete reaction with very little additional water. On the contrary, the traditional method requires a lot of water to dissolve the caustic soda, before mixing with the humic acid to form a paste state, followed by more complicated steps.

4. In the present invention, the flow pattern is very vigorous by thoroughly mixing the solid ingredients to achieve a rapid reaction, which can be completed in less than 20 minutes vs. 20-26 hours claimed by Patent CN101544675B.

5. Technical specification of the basic principle behind the present invention is due to (a) the large contact area of the ingredients created by the high-speed mixing and (b) the neutralization reaction carried out both on the surface and on the inside of the powders. In the meantime, the temperature rises rapidly, causing the caustic flake to melt and then to penetrate into the humic acid powders by osmotic pressure.

6. This invention uses the frictional heat and exothermic heat generated by the reactants to control the reaction, to obtain more stable quality, and most importantly, to save a lot of energy from steam injection. Additionally, since all the chemical reactions take place under fluidizing conditions, any excess water contained in the mixture of solid phase (~30% water) can be evaporated, thereby eliminating the subsequent product drying and grinding steps.

EXAMPLES

Three experimental tests were conducted under the setups in accordance with the concept described in this invention. Typical test conditions and the results obtained are shown in the following examples:

Example 1

Equipment: High speed intensive mixer (Henschel brand)
Capacity: 200-500 Liter Agitator speed: 500-1500 RPM
Recipe: Humic acid (Purity 44%, Water content 24%): 100 kg 90% Potassium hydroxide: 13.3 kg (feed slowly)
Product Analysis:

| Stirring Time, min | Water Content % | Soluble Humic Acid % |
|---|---|---|
| 5 | 20.3 | 24.5 |
| 10 | 18.7 | 26.8 |
| 15 | 16.4 | 29.2 |
| 20 | 14.3 | 31.5 |
| 30 | 13.1 | 35.9 |

Example 2

Equipment: High speed intensive mixer
Capacity: 200-500 Liter Agitator speed: 500-1500 RPM
Recipe: Humic acid (Purity 44%, Water content 24%): 100 kg 72% Sodium hydroxide: 12.6 kg (feed slowly)
Product Analysis:

| Stirring Time, min | Water Content % | Soluble Humic Acid % |
|---|---|---|
| 5 | 20.3 | 24.1 |
| 10 | 18.7 | 26.5 |

-continued

| Stirring Time, min | Water Content % | Soluble Humic Acid % |
|---|---|---|
| 15 | 16.4 | 28.9 |
| 20 | 14.8 | 31.1 |
| 30 | 12.7 | 35.5 |

Example 3

Equipment: High speed intensive mixer
Capacity: 200-500 Liter Agitator speed: 500-1500 RPM
Recipe: Humic acid (Purity 44%, Water content 24%): 100 kg 35% Ammonium hydroxide: 21 kg (under pressure spray mode)
Product Analysis:

| Stirring Time, min | Water Content % | Soluble Humic Acid % |
|---|---|---|
| 5 | 21.2 | 23.1 |
| 10 | 18.9 | 25.5 |
| 15 | 16.4 | 27.8 |
| 20 | 14.3 | 30.2 |
| 30 | 13.1 | 35.1 |

The invention claimed is:

1. A process for producing humic acid salt, the process comprising:
mixing alkali hydroxide with a humic acid source in a solid-phase reactor under fluidizing conditions to react humic acid in the source with the alkali hydroxide to produce humic acid salt,
wherein the alkali hydroxide comprises potassium hydroxide, sodium hydroxide, or both,
wherein the humic acid salt comprises potassium humate, sodium humate, or both,
wherein the solid-phase reactor comprises a mixer running at 300 to 2,000 RPM,
wherein the alkali hydroxide is introduced into the reactor in flake or powder form, and
wherein the mixer generates sufficient frictional heat to liquefy the alkali hydroxide.

2. The process according to claim 1, which comprises using the heat of reaction and the frictional heat to dry the humic acid salt.

3. The process according to claim 2, wherein the mixing, reaction, and drying takes place in the reactor.

4. The process according to claim 1, wherein the humic acid source comprises brown coal, peat, or weathering coal.

5. The process according to claim 1, wherein the fluidizing conditions are achieved without using a fluidizing gas.

6. The process according to claim 1, wherein the reaction is completed in less than 20 minutes.

7. The process according to claim 1, wherein the alkali hydroxide further comprises ammonium hydroxide and the humic acid salt further comprises ammonium humate.

8. The process according to claim 7, which further comprises recovering ammonia and water vapor from the reactor.

9. The process according to claim 7, which comprises spraying the ammonium hydroxide into the reactor.

10. The process according to claim 9, which comprises using the heat of reaction and the heat generated by friction to dry the humic acid salt.

11. The process according to claim 10, wherein the mixing, reaction, and drying takes place in the reactor.

* * * * *